United States Patent
Tydeman

(10) Patent No.: US 10,219,833 B2
(45) Date of Patent: Mar. 5, 2019

(54) OBSTETRIC DEVICE

(71) Applicant: Guy's and St Thomas' NHS Foundation Trust, London (GB)

(72) Inventor: Graham Stephen John Tydeman, Fife (GB)

(73) Assignee: GUY'S AND ST THOMAS' NHS FOUNDATION TRUST, London (GB)

(*) Notice: Subject to any disclaimer, the term of this patent is extended or adjusted under 35 U.S.C. 154(b) by 398 days.

(21) Appl. No.: 14/603,512

(22) Filed: Jan. 23, 2015

(65) Prior Publication Data

US 2016/0213401 A1    Jul. 28, 2016

(51) Int. Cl.
 A61B 17/42    (2006.01)
 A61B 17/00    (2006.01)
 A61B 90/00    (2016.01)

(52) U.S. Cl.
 CPC .... *A61B 17/42* (2013.01); *A61B 2017/00455* (2013.01); *A61B 2090/0811* (2016.02)

(58) Field of Classification Search
 CPC .......... A61B 17/42; A61B 2017/00455; A61B 2090/0811; A61B 17/442
 USPC ...................................................... 606/122
 See application file for complete search history.

(56) References Cited

U.S. PATENT DOCUMENTS

| 2,194,989 A | 3/1940 | Torpin |
| 5,224,947 A | 7/1993 | Cooper et al. |
| 5,810,840 A * | 9/1998 | Lindsay ............... A61B 17/442 606/122 |
| 2009/0182346 A1* | 7/2009 | Uddenberg .......... A61B 17/442 606/123 |
| 2012/0095476 A1 | 4/2012 | Porat et al. |
| 2013/0325027 A1 | 12/2013 | Leitch |

FOREIGN PATENT DOCUMENTS

| CN | 202027689 U | 9/2011 |
| EP | 1671599 A1 | 6/2006 |
| FR | 936977 A | 4/1948 |
| FR | 65209 E | 7/1956 |
| GB | 2302024 A | 1/1997 |
| WO | WO89/06112 A1 | 7/1989 |
| WO | WO2006/027731 A1 | 3/2006 |
| WO | WO2008/067204 A1 | 6/2008 |
| WO | WO2009/060431 A2 | 5/2009 |
| WO | WO 2011/058289 A1 | 5/2011 |
| WO | WO2012/042266 A1 | 4/2012 |

* cited by examiner

*Primary Examiner* — Eric J Rosen
*Assistant Examiner* — George J Ulsh
(74) *Attorney, Agent, or Firm* — Gordon & Jacobson, P.C.

(57) ABSTRACT

An obstetric device has a head piece having a flexible peripheral rim and a floor spaced from the flexible peripheral rim defining a cavity. One or more support lugs extend upwardly from the floor of the cavity; and an air communication aperture is provided in the floor of the cavity. Typically the device is formed a distal end piece having an orientation mark; and a tube interconnecting the head piece and the distal end piece.

19 Claims, 4 Drawing Sheets

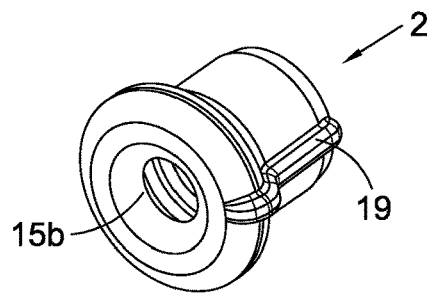
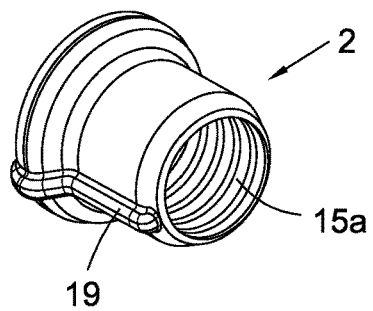
Fig. 4A          Fig. 4B
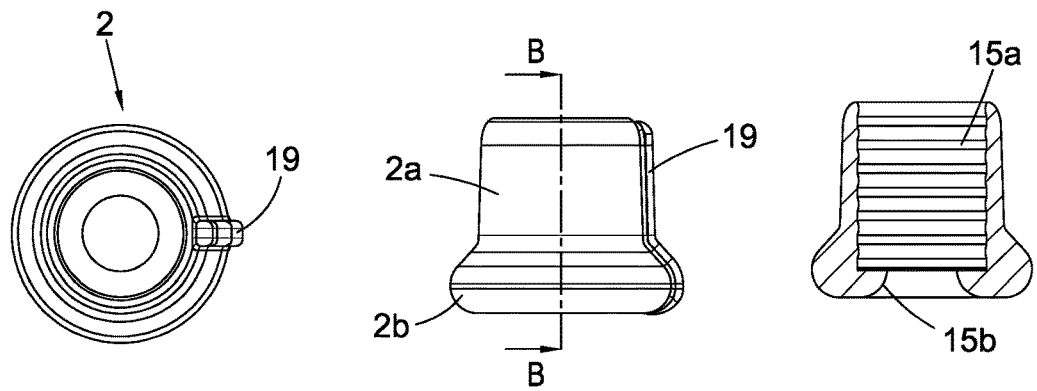
Fig. 4C          Fig. 4D          Fig. 4E
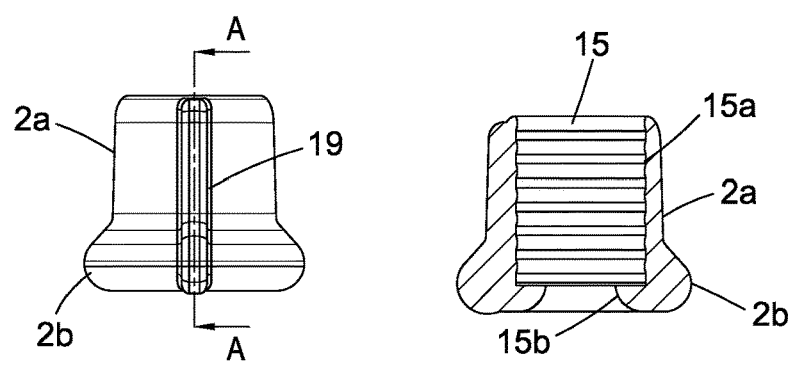
Fig. 4F          Fig. 4G

OBSTETRIC DEVICE

BACKGROUND

1. Field

This invention relates generally to an obstetric device, and more particularly to an obstetric device for use in birthing processes particularly birthing processes in which the baby is not delivered via the birthing canal.

2. Related Art

It is not uncommon during the birthing process for a pregnant woman to reach full dilation of the cervix and begin pushing the fetus down through the birth canal only to have the fetus become lodged in the birth canal. Often a vacuum or forceps may be used to further assist the delivery. This may, however, worsen the situation by causing the fetus to become more firmly impacted or lodged in the birth canal without achieving delivery. After attempts of vaginal delivery are abandoned, the delivering physician must deliver the fetus through caesarean section.

During the course of a caesarean section, the fetus must be positioned such that the physician can reach behind the head of the fetus to deliver the baby out of the uterine cavity through an incision made for purposes of delivery. Presently, the fetal head is often positioned for such delivery by an assisting physician or nurse. Such an assistant must insert his or her hand up through the birth canal and place his or her fingers against the fetal head to position the head such that the delivering physician can reach behind the head and gently deliver the baby out through the incision in the uterine cavity. Often in such cases, a surgical drape is placed over the legs of the patient and the assistant is essentially working blind under the sterile drape.

The assistant who asserts the force to push the fetal head into position for the delivering physician, operative or surgeon does so with his or her fingers, which requires considerable force and is limited by the length of the assistant's arms and/or fingers, as well as by the assistant's physical strength.

Obstetric devices have been proposed which have a head piece for contacting the baby's head and an elongate tube communicating with the device head piece. The device is introduced via the female vagina and birth canal and when contacting the baby's head permits air communication along the tube to a position below the baby's head. Examples of such devices are disclosed in for example US2013/0325027 or WO2011/058289.

SUMMARY

In accord with the present invention, an obstetrical device which provides for a more efficient and safe delivery of a fetus has now been devised.

In accordance with the present invention there is provided an obstetric device comprising a head piece having a flexible peripheral rim and a floor spaced from the flexible peripheral rim defining a cavity, one or more support lugs extending upwardly from the floor of the cavity; an air communication aperture being provided in the floor of the cavity.

In a preferred embodiment a plurality of support lugs are provided extending upwardly from the floor of the cavity, the support lugs being spaced from one another.

It is preferred that the peripheral rim has a peripheral wall extending to the floor of the cavity and the support lug or lugs are spaced from the peripheral wall. This enhances the general ability of the peripheral wall/rim to deform with respect to and independently of the support lugs In certain embodiments it is preferred that three or more (most preferably four) support lugs are distributed about a single or main communication aperture in the floor of the cavity.

It is preferred that the support lugs have respective inclined upper contact surfaces, preferably inclined toward the centre of the head piece. The contact surfaces are to provide a distributed contact network for contacting the baby's head.

In a preferred embodiment the upper most level of the lugs is positioned below the level of the flexible peripheral rim. The rim deforms under pressure allowing the contact surfaces of the lugs to contact and support the baby's head.

In a preferred embodiment the flexible peripheral rim has an outer, lead-in, inclined surface leading upwardly to an apex of the peripheral rim.

It is preferred that the flexible peripheral rim has an inner, inclined surface leading downwardly from an apex of the peripheral rim.

The nature and technical purpose of the inclined surfaces is described in more detail in relation to the exemplary embodiment.

The head piece may beneficially be provided with an integrally formed tube length communicating with the aperture.

It is preferred that the peripheral rim is inclined at an angle to the axis of the tube length.

It is preferred that the device further comprises an elongate tube extending from the head piece, positioned at a distal end of the tube, to a proximal end piece, the proximal end piece being secured to the proximal end of the tube and provided with a central bore and a positioning mark or formation provided on the exterior surface of the proximal end piece.

Beneficially, the positioning mark or formation comprises a relief formation (such as a ridge or groove).

The proximal end piece preferably includes wider bore portion connecting with a narrower bore portion, the wider bore formation having formations to enhance securing engagement with the outer surface of the tube.

It is preferred that the narrower bore portion has a diameter corresponding substantially to the bore of the tube.

It is preferred that the proximal end piece has a flared or bulbous termination and the positioning mark or formation is provided on the flared or bulbous termination.

According to a further aspect, the invention provides an obstetric device of multi part construction comprising at least:

a) a head piece for contacting a baby's head;
b) a proximal end piece having an orientation mark; and
c) a tube interconnecting the head piece and the proximal end piece.

It is preferred that the interconnecting tube is received in respective wide bore portions of the head piece and the proximal end piece and has an internal bore dimensioned to correspond to narrower internal bore portions of the head piece and the proximal end piece.

Beneficially the interconnecting tube is received in respective wide bore portions of the head piece and the proximal end piece, the wide bore portions being provided with gripping surface formations for gripping the outer surface of the interconnecting tube.

Preferably the interconnecting tube has a smooth outer surface.

Preferred features of the alternative aspects are of course mutually beneficial.

These and other aspects of the present invention will be apparent from and elucidated with reference to, the embodiment described herein.

An embodiment of the present invention will now be described, by way of example only, and with reference to the accompanying drawings.

BRIEF DESCRIPTION OF THE DRAWINGS

FIG. 3D is a view along the section B-B in FIG. 3E; FIG. 3G is a section along A-A in FIG. 3F; and FIG. 3C is a section along B-B in FIG. 3A;

FIGS. 4A to 4G are various views of the proximal end portion of the device of FIGS. 1 and 2; in particular, FIG. 4E is a section along B-B in FIG. 4D; and FIG. 4G is a section along A-A of FIG. 4F;

DETAILED DESCRIPTION OF THE PREFERRED EMBODIMENTS

Figure 1:
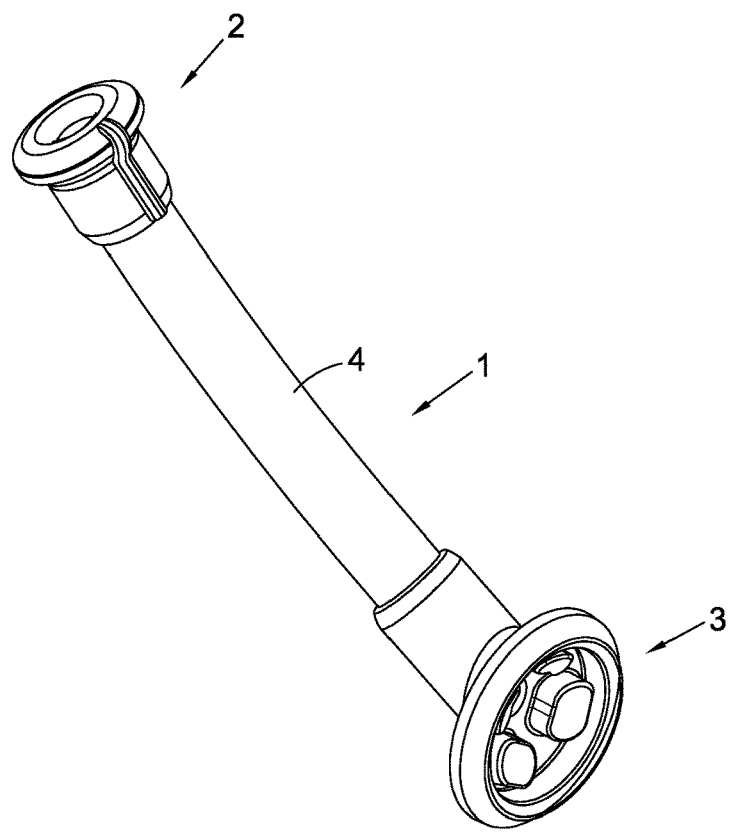
FIGS. 1 and 2 are different perspective views of an obstetric device in accordance with the invention.
Figure 2:
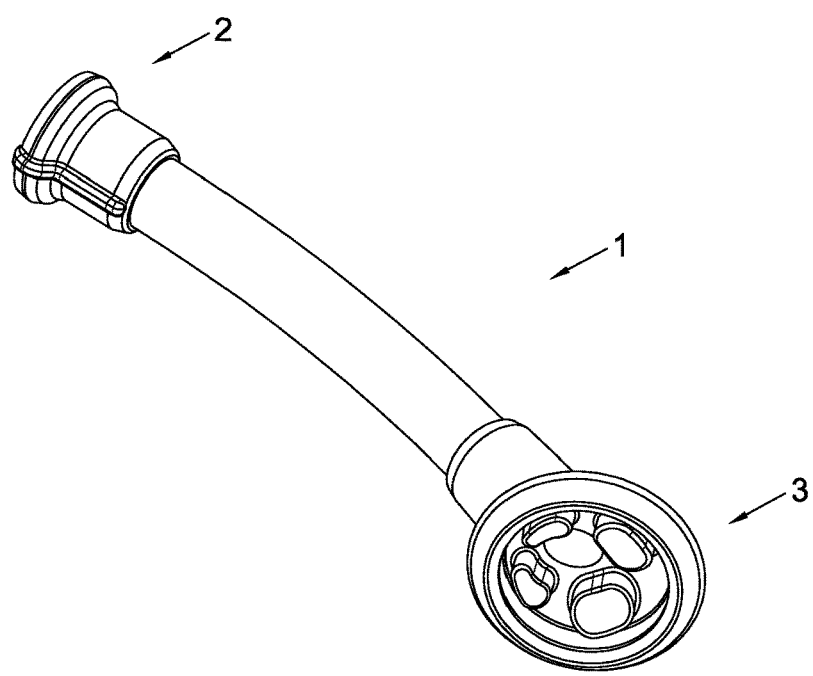

Referring to the drawings, the obstetric device 1 has certain general features in common with exemplary prior art devices such as those shown in for example US2013/0325027 or WO2011/058289. For example the devices have in common a proximal end portion 2 and a distal head portion 3 connected at either end of an elongate tube 4 having a longitudinally running hollow bore 5.

In accordance with the present invention the proximal end portion 2 and a distal head portion 3 are formed as separate pieces and connected at either end of the elongate tube 4. Each of the distal head piece 3, elongate tube 4, and a proximal end piece 2 are formed of platinum grade silicon 30/40 Shore.

Figure 3A:
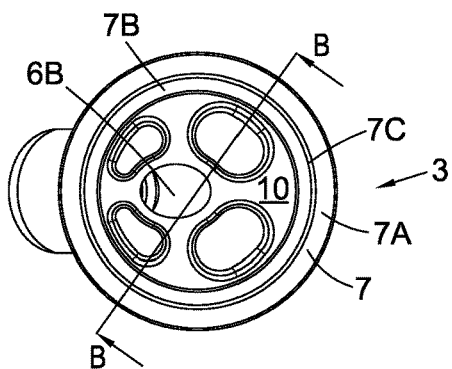
FIGS. 3A to 3G are various views of the distal head portion of the device of FIGS. 1 and 2, in particular
Figure 3B:
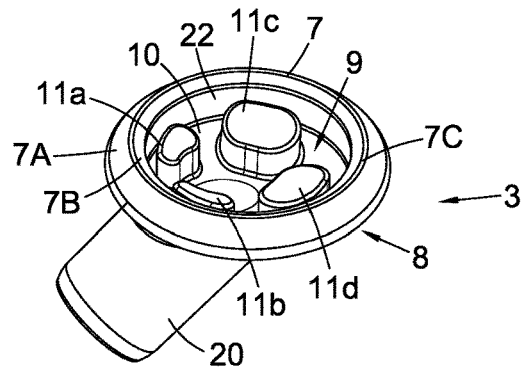
Figure 3C:
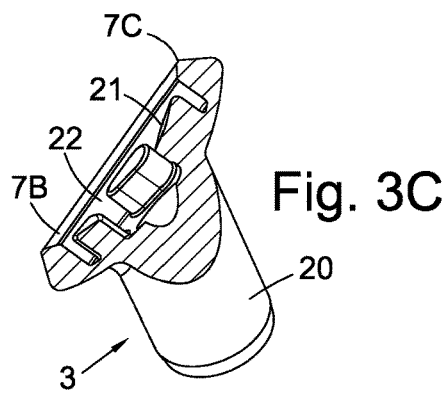
Figure 3D:
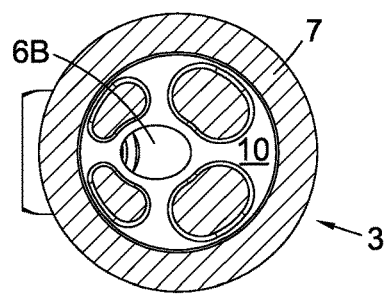
Figure 3E:
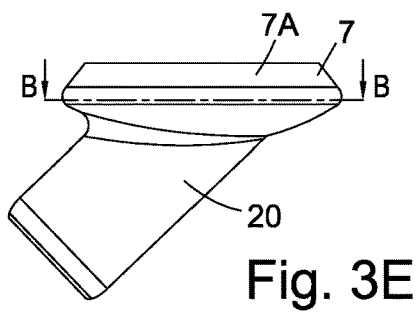
Figure 3F:
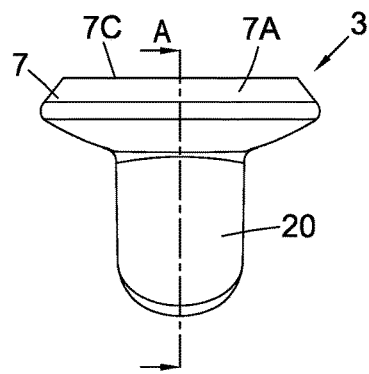
Figure 3G:
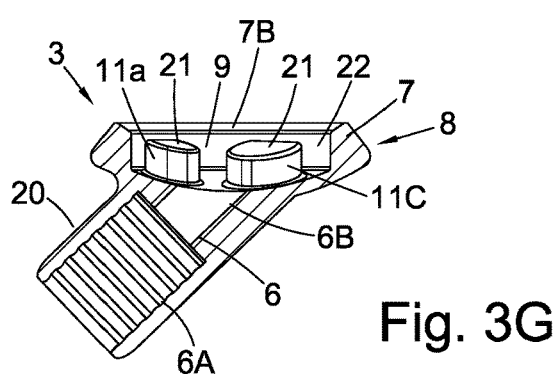
Figure 5:
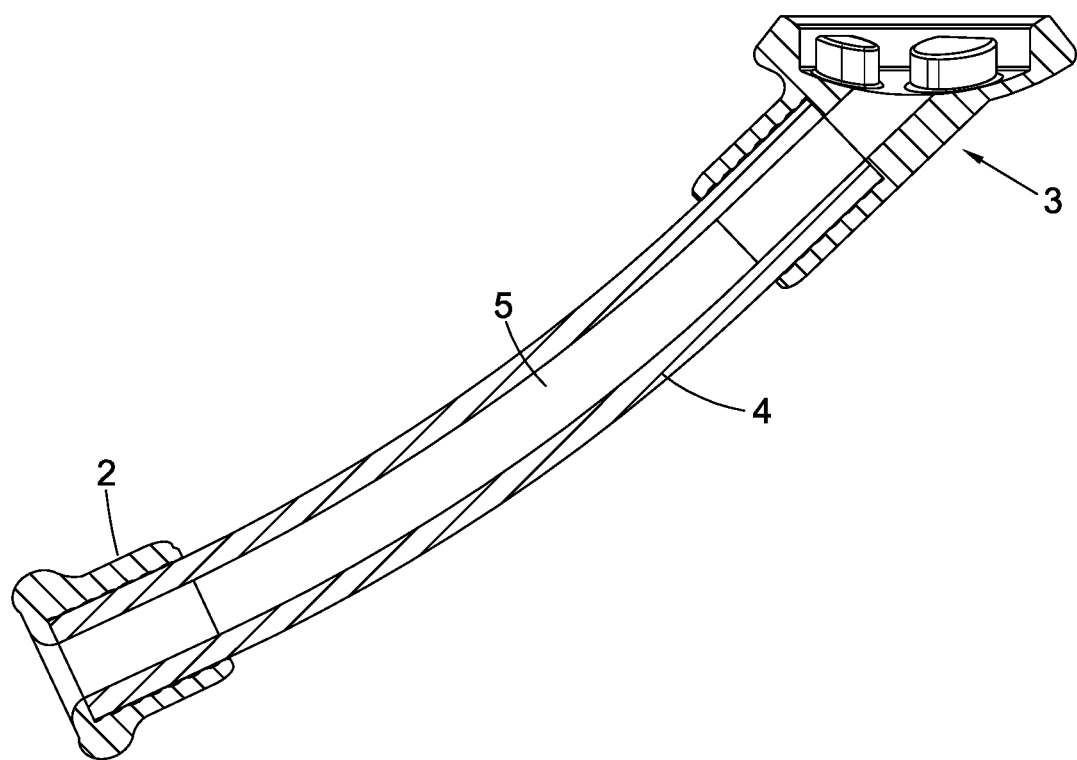
FIG. 5 is a longitudinal section of the assembled device.

Referring to FIGS. 3A to 3G, the head portion 3 has a stem 20 internally of which is provided a longitudinally running stepped bore 6 communicating with opposed ends having a wide bore portion 6A and a narrower bore portion 6B. Bore portion 6A has a profiled inner surface arranged to provide a grip fit about the external diameter of the interconnecting tube 4 at its end. The profiled inner surface of bore 6A includes a series of spaced arcuate ridge formations providing a secure connection, whilst enabling easy assembly of the device. The narrow bore portion 6B has a bore diameter corresponding to the internal bore 5 of the elongate interconnecting tube 4. At the distal-most portion of the head portion 3 is a contact pad 8 comprising an orbital rim 7 defining a cavity 9 having a floor 10 and upstanding from the floor 10 a plurality of lugs 11a, 11b, 11c, 11d. The lugs 11a, 11b, 11c, 11d have respective upper surface plateaus (see for example 21 in FIGS. 3C and 3G) positioned slightly below the level of the peripheral rim 7. The upper surface plateaus 21 of the lugs 11a, 11b, 11c, 11d are inclined from an upper edge proximate the peripheral rim 7 to a lower edge toward the centre of the contact pad 8. The bore 6 communicates with the floor 10 of the contact pad 8 at an aperture in the floor 10, and the lugs 11a, 11b, 11c, 11d are distributed about the aperture 6. The lugs 11a, 11b, 11c, 11d have upright walls which may be substantially parallel to and spaced from the perimeter wall 22 at the peripheral orbital rim 7. The contact pad 8 is provided at an acute angle (alpha) to the axis of the tube 4. The axis of the tube connector stem 20 of the head is angled with respect to the pad in order to achieve this.

The peripheral orbital rim 7 comprises outer and inner inclined surfaces 7a, 7b meeting at an apex 7c. This arrangement enables the physician's fingers to be guided first upwardly toward the baby's head along lead-in surface 7a and then downwardly along surface 7b under the baby's head when located by the pad 8. The apex 7b is also flexible such that when the baby's head is located it can collapse/deform downwardly such that the surfaces of the lugs 11a, 11b, 11c, 11d contact the baby's head in addition to the peripheral orbital rim 7.

Referring to FIGS. 4A to 4G, the proximal end portion 2 comprises a stepped bore 15 communicating with opposed ends having a wide bore portion 15a and a narrower bore portion 15b. Bore portion 15a has a profiled inner surface arranged to provide a grip or push fit about the external diameter of the interconnecting tube 4 at its end. The profiled inner surface of bore 15a includes a series of spaced arcuate ridge formations providing a secure connection, whilst enabling easy assembly of the device. The narrow bore portion 15b has a bore diameter corresponding to the internal bore 5 of the elongate interconnecting tube 4. The exterior profile of the end portion flares outwardly from a narrower neck 2a to a flared terminal end 2b of wider proportion. The outer surface is also provided with a longitudinally running orientation formation in the form of a ridge formation 19 which importantly extends to lie over the flared terminal end section 2b.

Instead of a longitudinally running ridge formation 19 a groove or other formation could be provided or even a non-profiled mark, in order to function as the orientation formation 19. However a formation having a tactile quality is preferred. The orientation formation 19 can be used to indicate the position of the head. An advantage of the present invention is that the proximal end portion can be fitted to the tube 4 in any angular position or orientation to suit the operative, such that the position of the head 3 is indicated by reference to the position of the orientation formation 19 but not interfering with the grip of the user in manipulating the device. For example, upon assembly, the formation could be positioned at the upper or lower surface or rotated through 90 degrees to the preference of the user. It is however important that once fitted the end portion does not rotate relative to the tube 4 once fitted. By having the orientation formation only on the end of the proximal end portion 2, the interconnecting tube 4 can have a smooth outer surface which is preferred from a comfort of use perspective and cleaning. The end piece 2 can be conveniently removed for cleaning.

In operation the device can be used in a similar fashion to the prior art devices described in for example US2013/0325027 or WO2011/058289. However specific advantages of the present invention lie in the following.

1. The soft silicon material of the device are atraumatic to mother and baby.
2. The 3 part construction of the device allows for ease of cleaning and assembly and permits the orientation formation 19 to be set at a position to the user's preference.
3. The provision of the orientation formation 19 on the proximal end portion only allows for ease of manufacture, improved hygiene and patient comfort as the interconnecting tube can have a smooth outer surface.

4. The provision of a central aperture on the pad 8 of the head portion allows for air to enter deep below the head.
5. The provision of the lugs with the inclined surfaces below the level of the orbital peripheral rim allows for good head support over a large area whilst leaving space for the physician's fingers in the cavity of the device head piece. The lugs also prevent introduction of material into the bore of the tube through the head piece pad 8.
6. The inclined lead-in surface 7a and the down surface 7b combined with the flexibility of the head piece pad 8 allow for ease of introduction of the physician's fingers.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. In the present specification, "comprises" means "includes or consists of" and "comprising" means "including or consisting of". The singular reference of an element does not exclude the plural reference of such elements and vice-versa. The mere fact that certain measures are recited in mutually different dependent claims does not indicate that a combination of these measures cannot be used to advantage.

The invention claimed is:

1. An obstetric device comprising:
   a head piece having:
      a contact pad comprising a flexible peripheral rim, a floor spaced from the flexible peripheral rim defining a cavity, and at least one support lug extending upwardly from the floor of the cavity and spaced from the flexible peripheral rim, wherein the at least one support lug has an inclined upper contact surface;
      an air communication aperture at a central position defined in the floor of the cavity to allow air to enter into the cavity, the at least one support lug being disposed around the central air communication aperture;
      a tube connector stem coupled to the contact pad and having a bore in communication with the aperture, wherein the tube connector stem is disposed at an acute angle to the contact pad;
   a tube connected at a distal end to the tube connector stem; and
   a manipulation grip connected to a proximal end of the tube.
2. The device according to claim 1, wherein a plurality of support lugs are provided extending upwardly from the floor of the cavity, the support lugs being spaced from one another.
3. The device according to claim 1, wherein three or more support lugs are distributed about the air communication aperture in the floor of the cavity.
4. The device according to claim 1, wherein an uppermost level of the at least one support lug is positioned below a level of the flexible peripheral rim.
5. The device according to claim 1, wherein the flexible peripheral rim has a peripheral wall extending to the floor of the cavity and the at least one support lug is spaced from the peripheral wall.
6. The device according to claim 1, wherein the flexible peripheral rim has an outer, lead-in, inclined surface leading upwardly to an apex of the peripheral rim.
7. The device according to claim 1, wherein the flexible peripheral rim has an inner, inclined surface leading downwardly from an apex of the peripheral rim.
8. The device according to claim 1, wherein the inclined upper contact surface is inclined toward the center of the head piece.
9. The device according to claim 8, wherein the tube is received in respective wide bore portions of the tube connector stem and of the manipulation grip, the wide bore portions being provided with gripping surface formations for gripping an outer surface of the tube.
10. The device according to claim 1, wherein the manipulation grip includes an orientation mark or formation provided on an exterior surface of the manipulation grip.
11. The device according to claim 10, wherein the orientation mark or formation comprises a relief formation.
12. The device according to claim 10, wherein the manipulation grip has a flared or bulbous termination and the orientation mark or formation is provided on the flared or bulbous termination.
13. The device according to claim 1, wherein the manipulation grip has one end that is configured to be fitted to the tube in any rotational orientation relative to the proximal end of the tube.
14. The device according to claim 1, wherein the manipulation grip includes a wider bore portion connecting with a narrower bore portion, the wider bore portion of the manipulation grip having formations to enhance securing engagement with an outer surface of the tube.
15. The device according to claim 14, wherein the narrower bore portion of the manipulation grip has a diameter corresponding to a bore of the tube.
16. The device according to claim 1, wherein the tube is received in respective wide bore portions of the tube connector stem and of the manipulation grip, and the tube has an internal bore dimensioned to correspond to narrower internal bore portions of the head piece and the manipulation grip.
17. An obstetric device comprising:
    a head piece having:
       a contact pad comprising a flexible peripheral rim, a floor spaced from the flexible peripheral rim defining a cavity, and at least one support lug extending upwardly from the floor of the cavity and spaced from the flexible peripheral rim;
       an air communication aperture at a central position defined in the floor of the cavity to allow air to enter into the cavity, the at least one support lug being disposed around the central air communication aperture;
       a tube connector stem coupled to the contact pad and having a bore in communication with the aperture, wherein the tube connector stem is disposed at an acute angle to the contact pad;
    a tube connected at a distal end to the tube connector stem; and
    a manipulation grip connected to a proximal end of the tube, wherein the manipulation grip includes a wider bore portion connecting with a narrower bore portion, the wider bore portion of the manipulation grip having formations to enhance securing engagement with an outer surface of the tube.

18. The device according to claim 17, wherein the narrower bore portion of the manipulation grip has a diameter corresponding to a bore of the tube.

19. An obstetric device comprising:
   a head piece having:
      a contact pad comprising a flexible peripheral rim, a floor spaced from the flexible peripheral rim defining a cavity, and at least one support lug extending upwardly from the floor of the cavity and spaced from the flexible peripheral rim;
      an air communication aperture at a central position defined in the floor of the cavity to allow air to enter into the cavity, the at least one support lug being disposed around the central air communication aperture;
      a tube connector stem coupled to the contact pad and having a bore in communication with the aperture, wherein the tube connector stem is disposed at an acute angle to the contact pad;
   a tube connected at a distal end to the tube connector stem; and
   a manipulation grip connected to a proximal end of the tube, wherein the tube is received in respective wide bore portions of the tube connector stem and of the manipulation grip, and the tube has an internal bore dimensioned to correspond to narrower internal bore portions of the head piece and the manipulation grip.

* * * * *